(12) United States Patent
Higuchi et al.

(10) Patent No.: US 11,033,346 B2
(45) Date of Patent: Jun. 15, 2021

(54) MEDICAL MASTER-SLAVE MANIPULATOR SYSTEM

(71) Applicant: OLYMPUS CORPORATION, Tokyo (JP)

(72) Inventors: Tatsuya Higuchi, Yokohama (JP); Toshihiro Yoshii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 975 days.

(21) Appl. No.: 15/677,696

(22) Filed: Aug. 15, 2017

(65) Prior Publication Data

US 2017/0340398 A1    Nov. 30, 2017

Related U.S. Application Data

(63) Continuation of application No. PCT/JP2016/050801, filed on Jan. 13, 2016.

(30) Foreign Application Priority Data

Feb. 26, 2015   (JP) .............................. JP2015-037287

(51) Int. Cl.
| | |
|---|---|
| *A61B 34/37* | (2016.01) |
| *A61B 34/30* | (2016.01) |
| *A61B 34/00* | (2016.01) |
| *B25J 3/04* | (2006.01) |
| *A61B 34/20* | (2016.01) |

(52) U.S. Cl.
CPC .............. *A61B 34/37* (2016.02); *A61B 34/30* (2016.02); *A61B 34/70* (2016.02); *A61B 34/71* (2016.02); *B25J 3/04* (2013.01); *A61B 34/20* (2016.02); *A61B 2034/301* (2016.02)

(58) Field of Classification Search
CPC ........................................................ B25J 3/04
See application file for complete search history.

(56) References Cited

U.S. PATENT DOCUMENTS

| | | | |
|---|---|---|---|
| 2009/0253959 A1 | 10/2009 | Yoshie et al. | |
| 2017/0151028 A1* | 6/2017 | Ogawa | ................... A61B 34/32 |
| 2017/0360519 A1* | 12/2017 | Yorimoto | ........... A61B 1/00039 |

FOREIGN PATENT DOCUMENTS

| | | |
|---|---|---|
| EP | 2 601 905 A1 | 6/2013 |
| JP | 2009-247619 A | 10/2009 |
| JP | 2010-35874 A | 2/2010 |
| JP | 2012-55576 A | 3/2012 |
| WO | 2014/021122 A1 | 2/2014 |

OTHER PUBLICATIONS

International Search Report issued in PCT/JP2016/050801 dated Mar. 29, 2016 (in English and Japanese).
Extended Supplementary European Search Report dated Jul. 26, 2018 in European Patent Application No. 16 75 5056.5.

* cited by examiner

*Primary Examiner* — Vicky A Johnson
(74) *Attorney, Agent, or Firm* — Scully, Scott, Murphy & Presser, P.C.

(57) ABSTRACT

A correction jig of a medical master-slave manipulator system limits a straight state of a master manipulator, in a state where the correction jig is attached to the master manipulator.

9 Claims, 7 Drawing Sheets

MEDICAL MASTER-SLAVE MANIPULATOR SYSTEM

TECHNICAL FIELD

This application is a continuation application based on a PCT Patent Application No. PCT/JP2016/050801, filed on Jan. 13, 2016, whose priority is claimed on Japanese Patent Application No. 2015-037287, filed in Japan on Feb. 26, 2015. The contents of both the PCT Application and the Japanese Application are incorporated herein by reference.

BACKGROUND ART

In the related art, a medical manipulator system using a master-slave method is known (for example, refer to Japanese Unexamined Patent Application, First Publication No. 2009-247619 and Japanese Unexamined Patent Application, First Publication No. 2010-035874).

The medical manipulator system using the master-slave method operates a slave manipulator in accordance with an operation performed on a master manipulator. In the medical manipulator system using the master-slave method, the slave manipulator needs to properly follow a position or an orientation of the master manipulator.

Therefore, for example, in the system disclosed in Japanese Unexamined Patent Application, First Publication No. 2009-247619 and Japanese Unexamined Patent Application, First Publication No. 2010-035874, it is preferable that calibration is performed to maintain following accuracy of the slave manipulator which follows the master manipulator.

SUMMARY OF INVENTION

According to a first aspect of the present invention, a slave manipulator which has an end effector and a joint; a master manipulator which has a joint having a shape similar to the joint of the slave manipulator, and which receives an operation input for operating the slave manipulator; a control unit that generates an operation command for operating the slave manipulator based on the operation input to the master manipulator, and outputs the operation command to the slave manipulator; an overtube which has a tubular shape and into which the slave manipulator is inserted; and a correction jig that has a shape similar to at least a portion of the overtube so as to correct the master manipulator into a shape following an internal shape of the overtube, and that is attachable to the master manipulator. In a state where the correction jig is attached to the master manipulator, the correction jig limits the joint of the master manipulator to be a straight state.

According to a second aspect of the present invention, in the medical master-slave manipulator system according to the first aspect, when the control unit detects that the correction jig is attached to the master manipulator, the control unit lay generate the operation command for relatively moving the slave manipulator and the overtube so that the slave manipulator moves into the overtube and may output the operation command to the slave manipulator. In a state where the slave manipulator is located inside the overtube and the correction jig is attached to the master manipulator, the control unit may set a position of the joint of the slave manipulator which corresponds to the joint of the master manipulator, as an origin position of the joint in the slave manipulator.

According to a third aspect of the present invention, in the medical master-slave manipulator system according to the first aspect, the correction jig may have a channel member that holds the joint of the master manipulator to be a shape following a shape of the joint of the slave manipulator arranged inside the overtube, and a base that moves the channel member with respect to the master manipulator.

According to a fourth aspect of the present invention, in the medical master-slave manipulator system according to the first aspect, the correction jig may have a channel member that holds the joint of the master manipulator to be a shape following a shape of the joint of the slave manipulator arranged inside the overtube, and a base that holds the channel member. The master manipulator may be movable to the channel member so that at least the joint of the master manipulator is attached to the channel member.

According to a fifth aspect of the present invention, in the medical master-slave manipulator system according to the fourth aspect, the master manipulator may have a work table and a master arm that has an input unit which corresponds to the end effector, and the joint of the master manipulator. The channel member may be arranged on the work table so as to be relatively movable with respect to the master arm and so as to be capable of being fixed to the master arm in a state where the master arm is positioned with respect to the work table.

According to a sixth aspect of the present invention, in the medical master-slave manipulator system according to the first aspect, the correction jig may have a channel member into which the master manipulator is capable of being inserted and which has a shape similar to the overtube, and a rotation amount measurement portion which is configured to measure a rotation amount of the master manipulator rotating in a circumferential direction of the channel member in the channel member.

According to a seventh aspect of the present invention, in the medical master-slave manipulator system according to the first aspect, when the control unit is actuated, the control unit may determine whether or not the correction jig is in a positional relationship that the correction jig is attached to the master manipulator. In a case where the correction jig is not in a positional relationship that the correction jig is attached to the master manipulator, the control unit may stop controlling the slave manipulator until the correction jig is in the position relationship that the correction jig is attached to the master manipulator.

According to an eighth aspect of the present invention, a medical master-slave manipulator system in which an operation for operating the slave manipulator including an end effector and a slave joint is input, the medical master-slave manipulator system includes a first arm which is formed in a rod shape, a second arm which is formed in a rod shape, a master joint which is connected to the first an and the second arm such that the first arm and the second arm are capable of bending with respect to each other, and a correction jig which limits a bend of the second arm with respect to the first arm.

According to a ninth aspect of the present invention, in the medical master-slave manipulator system according to the eighth aspect, the correction jig may include a tube in which the first arm and the second arm are capable of being inserted. The correction jig may limit the bend of the second arm with respect to the first arm by the first arm and the second arm being inserted into the tube.

DESCRIPTION OF EMBODIMENTS

First Embodiment

Figure 1:
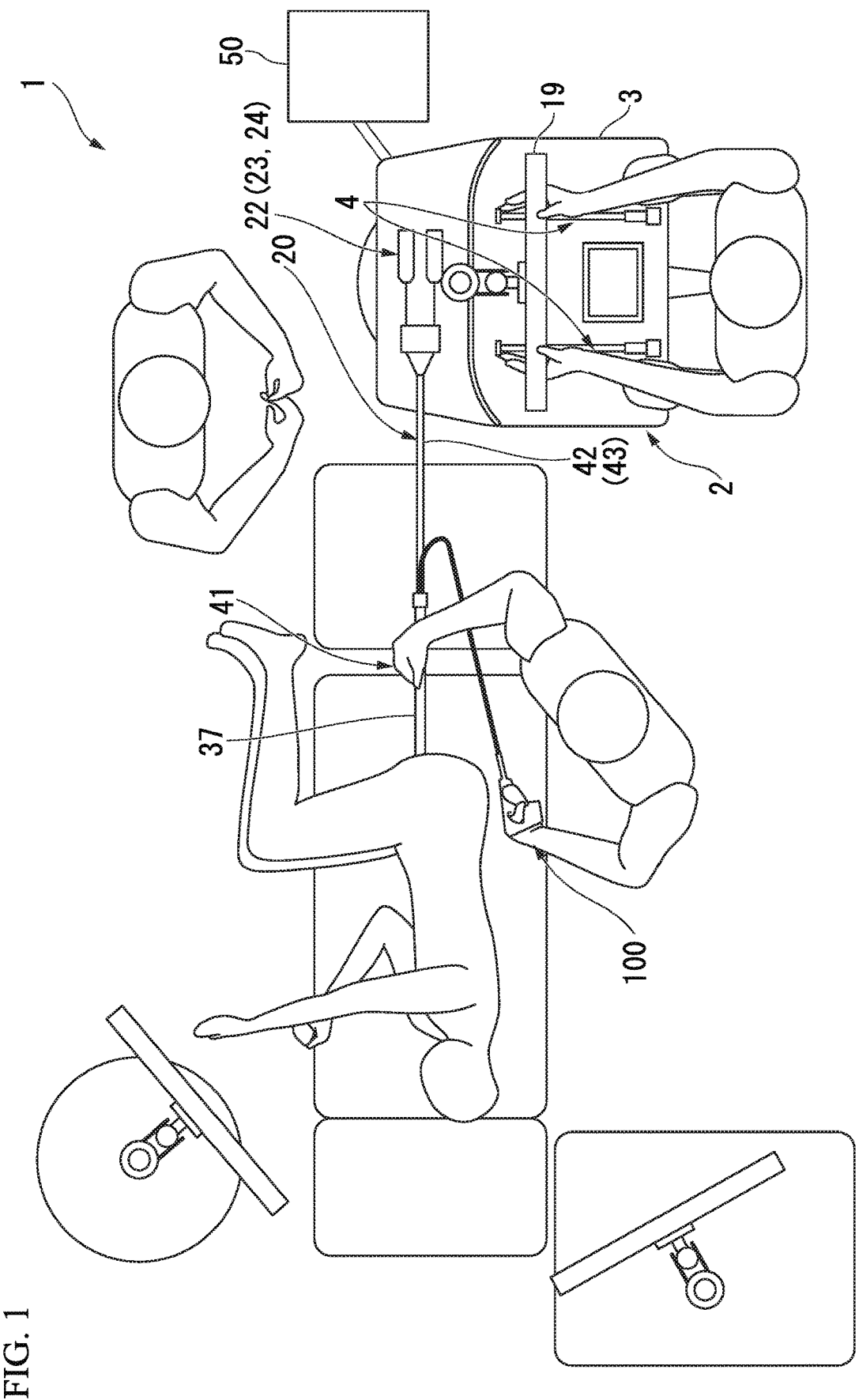
FIG. 1 is an overall view of a medical master-slave manipulator system according to a first embodiment of the present invention.
Figure 2:
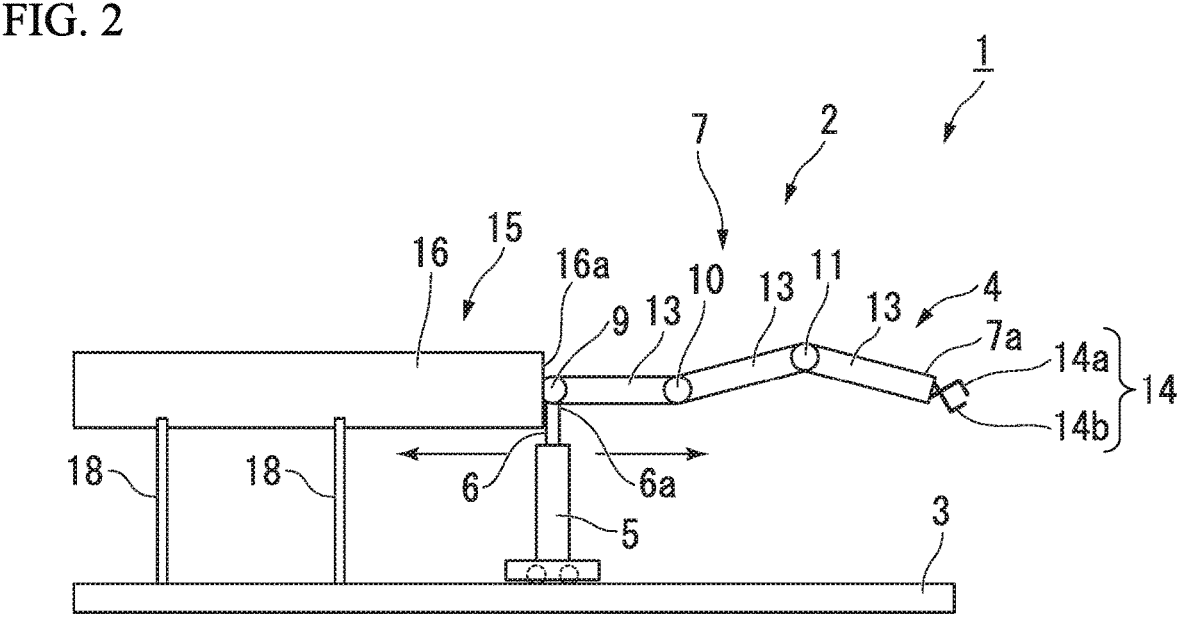
FIG. 2 is a schematic view illustrating a portion of a master manipulator of the manipulator system.
Figure 3:
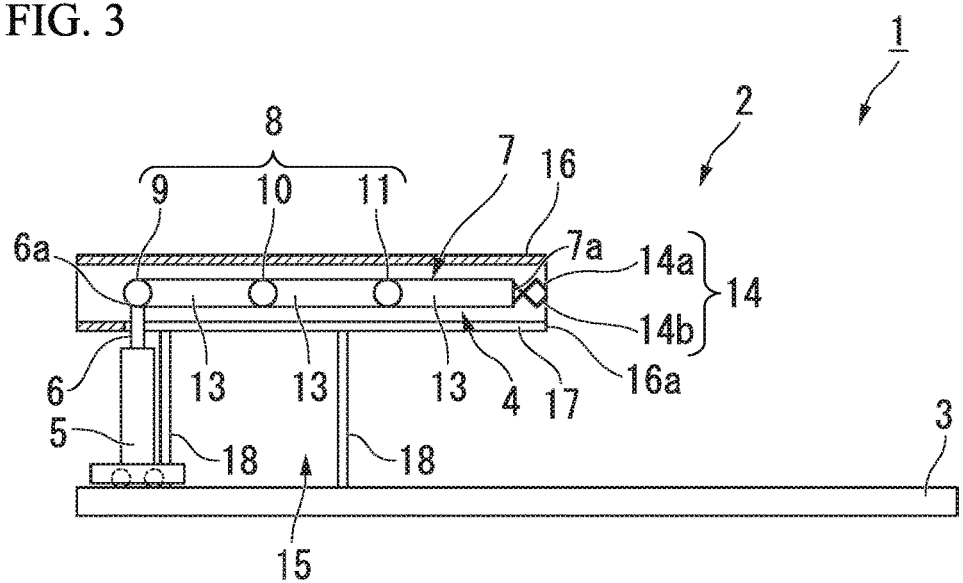
FIG. 3 is a partial sectional view schematically illustrating a portion of the master manipulator.
Figure 4:
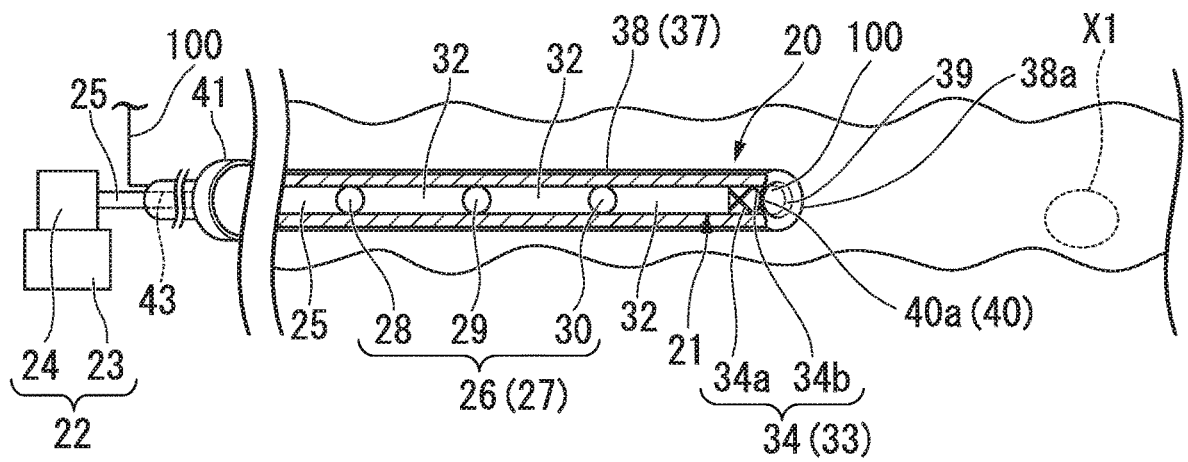
FIG. 4 is a view illustrating a portion of a slave manipulator of the manipulator system, and is a schematic sectional view illustrating a state where a portion of the slave manipulator is inserted into a body.
Figure 5:
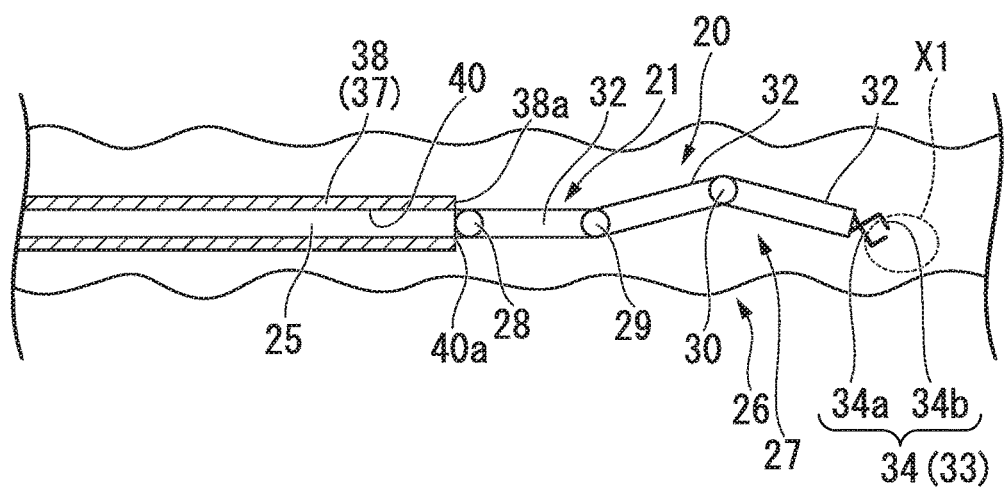
FIG. 5 is a partial sectional view schematically illustrating a process of treatment using an end effector of the slave manipulator.

A first embodiment according to the present invention will be described. FIG. 1 is an overall view of a medical master-slave manipulator system according to the present bodiment. FIG. 2 is a schematic view illustrating a portion of a master manipulator of the anipulator system. FIG. 3 is a partial sectional view schematically illustrating a portion of the master manipulator. FIG. 4 is a view illustrating a portion of a slave manipulator of the manipulator system, and is a schematic sectional view illustrating a state where a portion of the slave manipulator is inserted into a body. FIG. 5 is a partial sectional view schematically illustrating a process of treatment using an end effector of the slave manipulator.

As shown in FIG. 1, a medical master-slave manipulator system I (hereinafter, simply referred to as a manipulator system 1) according to the present embodiment has a master manipulator 2, a slave manipulator 20, and a control unit 50.

As shown in FIGS. 1 to 3, the master manipulator 2 includes a work table 3, a master arm 4, a master overtube 15, and a display device 19.

The master arm 4, the roaster overtube 15, and the display device 19 are attached to the work table 3.

The master arm 4 includes a pedestal 5, a shall 6, a master joint 7, and an input unit 14.

The pedestal 5 is connected to or placed on the work table 3 so as to be movable in a predetermined straight direction with respect to the work table 3. In addition, the pedestal 5 is connected to the shaft 6 of the master arm 4.

The shaft 6 is a rod shape member or tubular member which is capable of being inserted into a channel member 16 of the master overtube 15.

The master joint 7 is connected to an end (hereinafter, this end is referred to as a distal end 6a of the shaft 6) opposite to an end connected to the pedestal 5 in both ends of the shaft 6. The master joint 7 has a plurality of joint elements 8. In the present embodiment, the master joint 7 has a first joint element 9, a second joint element 10, and a third joint element 11 in this order from the distal end 6a of the shaft 6 toward the input unit 14. Each of the joint elements 8 arranged in the master joint 7 is connected by a rod-shaped arm element 13.

The first joint element 9, the second joint element 10, and the third joint element 11 are movably bent or rotated corresponding to a predetermined axis by a force transmitted to the master joint 7 via the input unit 14 from an operator inputting an input to the input unit 14. The first joint element 9, the second joint element 10, and the third joint element 11 are operated mutually independently or in conjunction with each other so as to deform the master joint 7 in response to the operation performed on the input unit 14. The first joint element 9, the second joint element 10, and the third joint element 11 have position information acquisition portion such as an encoder (not shown). The control unit 50 is configured so as to be capable of acquiring an operation amount when the first joint element 9, the second joint element 10, and the third joint element 11 are moved by the force transmitted from the input unit 14.

The input unit 14 is arranged at an end (hereinafter, this end is referred to as a distal end 7a of the master joint 7) opposite to an end connected to the distal end 6a of the shaft 6 in both ends of the master joint 7.

The input unit 14 can be moved with a hand of an operator. The input unit 14 may be configured so that the end effector 33 can be operated corresponding to a configuration of the end effector 33 (refer to FIG-S. 4 and 5) arranged in the slave arm 21.

As an example, in the present embodiment, for example, in a case where the end effector 33 has grasping forceps 34 that is capable of grasping a treatment target, the input unit 14 is configured so that a grasping operation of the treatment target can be input thereto corresponding to the grasping forceps 34 of the end effector 33. In addition, the input unit 14 may have a shape similar to a shape of the end effector 33. For example, in a case where the end effector 33 has the grasping forceps 34, a pair of input pieces 14a and 14b which can be opened and closed similarly to a pair of openable and closable forceps pieces 34a and 34b configuring the grasping forceps 34 may be arranged in the input unit 14. In this case, the pair of input pieces 14a and 14b has motion detection portion such as an encoder (not shown) capable of detecting open and close states. The control unit 50 is configured so as to be capable of acquiring an operation amount when the pair of input pieces 14a and 14b is moved by the operator.

The master overtube 15 has the tubular channel member 16 following a shape in the vicinity of a distal end 38a of a tube body 38 of a slave overtube 37 (to be described later), and a fixing portion 18 which fixes the channel member 16 to the work table 3. In addition, the master overtube 15 has master movement detection portion such as an encoder (not shown) for detecting a position or a movement amount of the master arm 4 with respect to the master overtube 15. The master overtube 15 has a shape similar to at least a portion of the tube body 38 so as to correct the master manipulator 2 into a shape following an internal shape of the tube body 38.

The shaft 6, the master joint 7, and the input unit 14 of the master arm 4 can be inserted into the channel member 16 shown in FIG. 3. The channel member 16 has a substantially tubular shape having a C-shaped cross section. A center line of the channel member 16 is straight.

In the channel member 16, a slit 17 into which the shaft 6 of the master arm 4 is inserted is formed extending in a direction along the center line of the channel member 16. It is preferable that an opening width of the slit 17 is a dimension which enables the shaft 6 of the master arm 4 to be advanced and retracted, and is a dimension which enables an inner surface of the channel member 16 to substantially surround an outer periphery of the master joint 7 and the end effector 33. If the opening width of the slit 17 is narrower to such an extent that the shaft 6 can suitably be advanced and retracted, the master arm 4 arranged inside the channel member 16 can have a straight shape which accurately follows the slave arm 21 arranged inside the slave overtube 37.

The master overtube 15 according to the present embodiment including the channel member 16 corrects the master joint 7 so that the master joint 7 is in a straight state in a state where the master joint 7 is located inside the channel member 16 of the master overtube 15. That is, the master overtube 15 according to the present embodiment is a correction jig which corrects the master joint 7 into the straight state.

The display device 19 shown in FIG. 1 displays an image captured by an endoscope 100 attachable to the slave manipulator 20, and displays various kinds of information output from the control unit 50 of the manipulator system 1.

As shown in FIGS. 1, 4, and 5, the slave manipulator 20 includes the slave arm 21 and the slave overtube 37, The slave an 21 includes a drive unit 22, an elongated member 25, a slave joint 26, and an end effector 33.

The drive unit 22 is arranged in an end portion of the elongated member 25 so as to operate the slave joint 26. The drive unit 22 has a power source unit 23 attached to the work table 3 of the master manipulator 2, and a attaching and detaching portion 24 which is attachable to and detachable from the power source unit 23 and which is fixed to the end portion of the elongated member 25. In the present embodiment, configuration elements ranging from the attaching and detaching portion 24 to the end effector 33 in the overall slave arm 21 can be attached to and detached from the slave overtube 37 and the power source unit 23.

The power source unit 23 generates power for operating the slave joint 26 in accordance with an operation command issued by the control unit 50.

In addition, the power source unit 23 can be advanced and retracted with respect to the work table 3. Since the power source unit 23 is advanced and retracted with respect to the work table 3, a position of the end effector 33 in the distal end of the slave arm 21 can be adjusted with respect to a second lumen 40. In addition, the work table 3 and the power source unit 23 are configured so that advancing and retracting operations of the power source unit 23 on the work table 3 correspond to the advancing and retracting operations of the master arm 4 arranged in the work table 3. Therefore, since the master arm 4 is moved with respect to the work table 3, the slave arm 21 can be advanced and retracted with respect to the second lumen 40.

A configuration may be adopted in which the drive unit 22 can operate the end effector 33. For example, in a case where the slave arm 21 has the grasping forceps 34 as the end effector 33, in accordance with the operation performed on the pair of input pieces 14a and 14b by the input unit 14, the drive unit 22 operates the pair of forceps pieces 34a and 34b of the grasping forceps 34 by portion of wire driving, for example.

The attaching and detaching portion 24 is a member detachable with respect to the power source unit 23 in order to transmit power generated by the power source unit 23 to the slave joint 26 via a wire (not shown). For example, the attaching and detaching portion 24 has an input shaft (not shown) meshing with an output shaft (not shown) of the power source unit 23 at any optional position. A power transmission path from the power source unit 23 to the slave joint 26 is configured depending on a relationship that the attaching and detaching portion 24 is mounted on the power source unit 23.

The elongated member 25 is a flexible or rigid member which can be inserted into the body. For example, in a case where the elongated member 25 is a member to be inserted into the gastrointestinal tract, the elongated member 25 is flexible so that the elongated member 25 can be inserted while being bent along the bent shape of the gastrointestinal tract.

Corresponding to the configuration of the master joint 7, the slave joint 26 has a plurality of transformable joint elements 27 following the deformation of the master joint 7, and an arm element 32 for connecting the joint elements 27 to each other. The slave joint 26 according to the present embodiment has a first joint element 28, a second joint element 29, and a third joint element 30 in this order from the elongated member 25 toward the end effector 33.

The first joint element 28, the second joint element 29 and the third joint element 30 can be operated independently of each other since power is transmitted from the drive unit 22 via a wire (not shown). For example, the first joint element 28 of the slave joint 26 is operated to follow the movement of the first joint element 9 when the first joint element 9 of the master joint 7 is moved by the operation performed on the input unit 14.

The end effector 33 is connected to the slave joint 26 in order to observe or treat a treatment target region inside a body. The end effector 33 may be an imaging unit including an image sensor, a treatment unit for incising or suturing the treatment target region, or a grasping unit for grasping a tissue of the treatment target region. A configuration of the end effector 33 is not particularly limited. For example, the end effector 33 according to the present embodiment has the grasping forceps 34 capable of grasping a living body tissue.

The grasping forceps 34 has the pair of forceps pieces 34a and 34b which are capable of opening and closing operations. The pair of forceps pieces 34a and 34b are connected to the attaching and detaching portion 24 of the drive unit 22 by wires (not shown), and are operated by the power transmitted from the drive unit 22 via the attaching and detaching portion 24. The operation of the pair of forceps pieces 34a and 34b is performed based on an operation command issued to the drive unit 22 by the control unit 50 in response to an operation performed on the input unit 14 by an operator.

The slave overtube 37 has a tube body 38, an operation unit 41, and a connection portion 42.

The tube body 38 is a tubular member having a first lumen 39 and the second lumen 40. The tube body 38 may be rigid or flexible. For example, in a case where the tube body 38 is inserted into a gastrointestinal tract, the tube body 38 is flexible and transformable to follow a bent shape of the gastrointestinal tract.

The known endoscope 100 arranged as a portion of the manipulator system 1 according to the present embodiment can be attached to the first lumen 39 of the tube body 38.

The elongated member 25, the slave joint 26, and the end effector 33 of the slave arm 21 can be inserted into the second lumen 40 of the tube body 38. In the present embodiment, a plurality of the slave arms 21 can be attached to the tube body 38. For this reason, a plurality of the second lumens 40 (two in the present embodiment, for example) are formed in the tube body 38.

The operation unit 41 is a portion grasped by an operator so as to advance and retract the tube body 38 or to rotate the tube body 38, and is arranged in a proximal end 38b of the tube body 38. The connection portion 42 for extending the second lumen 40 of the tube body 38 to the master manipulator 2 is attached to the operation unit 41.

The connection portion 42 has an extension lumen 43 into which a portion of the elongated member 25 of the slave arm 21 is inserted. The extension lumen 43 of the connection portion 42 is formed in the connection portion 42 corresponding to the configuration of the second lumen 40 of the tube body 38.

The control unit 50 shown in FIG. 1 generates an operation command for operating the power source unit 23 in response to an input operation performed on the input unit 14 of the master manipulator 2, and outputs the operation command to the power source unit 23. In addition, the control unit 50 can perform calibration for optimizing association between the slave manipulator 20 and the master manipulator 2. For example, the control unit 50 sets an initial position for associating with a positional relationship between the master joint 7 and the slave joint 26, and stores the initial position.

Figure 6:
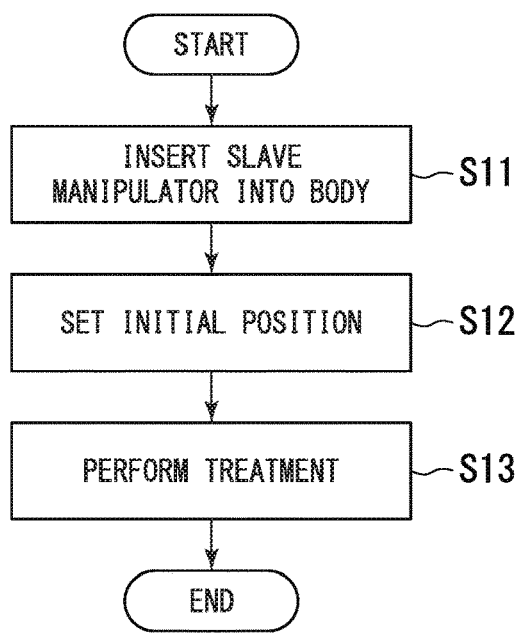
FIG. 6 is a flowchart illustrating a treatment flow using the anipulator system.
Figure 7:
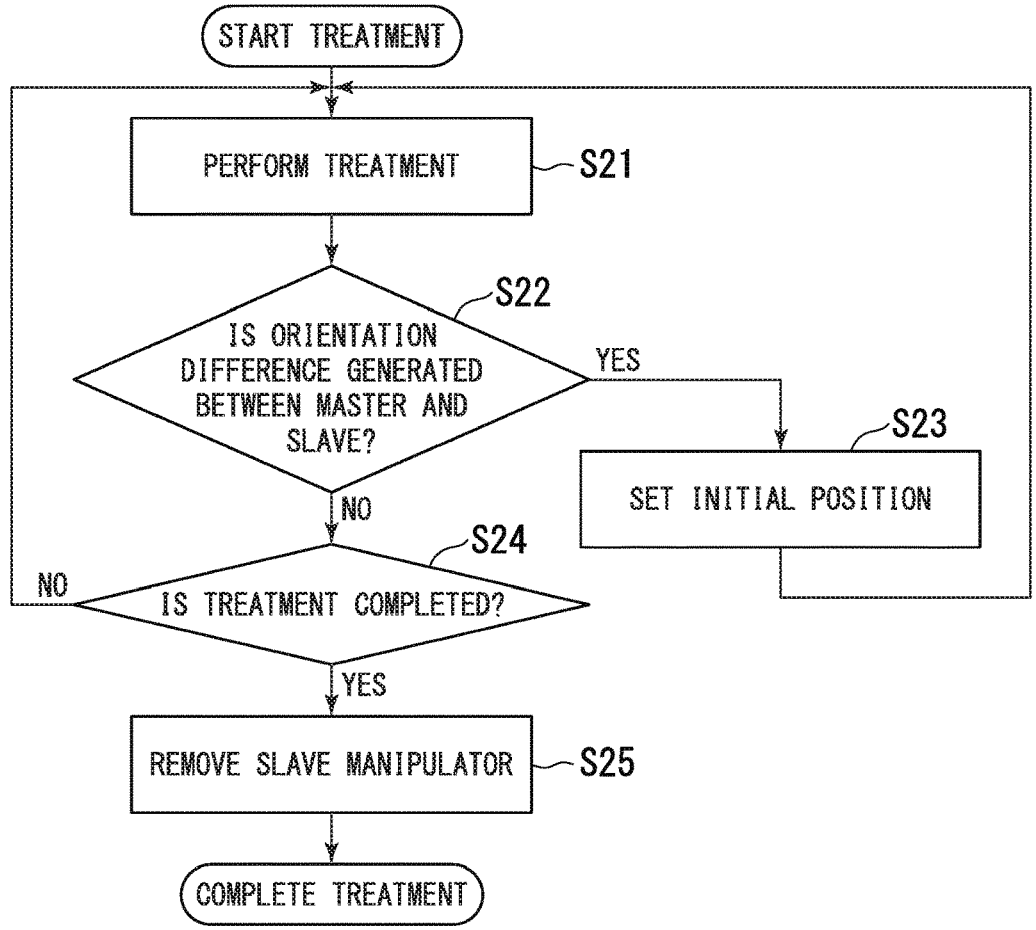
FIG. 7 is a flowchart illustrating a work flow in a case of setting an initial position of the slave manipulator during the treatment using the manipulator system.
Figure 8:
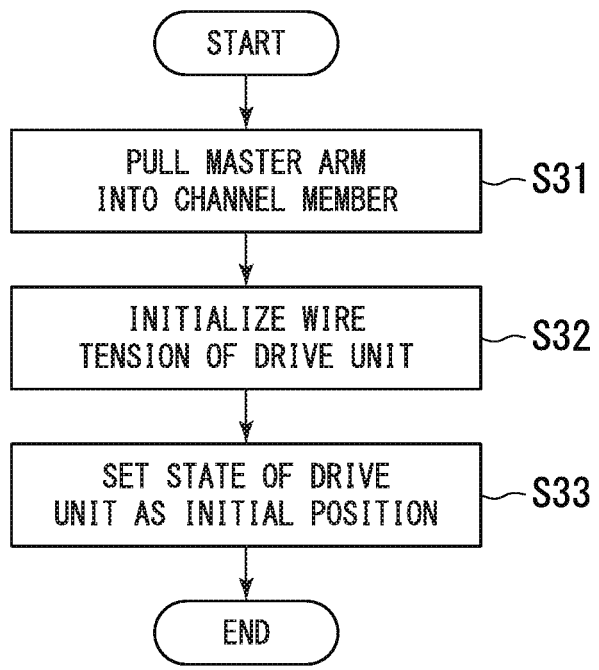
FIG. 8 is a flowchart illustrating an example of a setting procedure of the initial position in the manipulator system.

As an example of the calibration performed in the control unit 50, a procedure for setting the initial position of the slave joint 26 will be described. FIG. 6 is a flowchart illustrating a treatment flow using the manipulator system 1 according to the present embodiment. FIG. 7 is a flowchart illustrating a work flow in a case where the initial position of the slave manipulator 20 is set during the treatment using the manipulator system 1. FIG. 8 is a flowchart illustrating an example of the procedure for setting the initial position in the manipulator system 1.

According to the present bodiment, for example, when the manipulator system 1 is initially actuated or actuated again, or when an operator feels uncomfortable at the operation of the slave joint 26 while the manipulator system 1 is used, the operator can set the initial position.

In addition, in a case where the slave manipulator 20 is inserted into a complexly bent site in a body, a path length of a wire extending from the drive unit 22 to the slave joint 26 is changed due to the deformation of the slave manipulator 20 in some cases. In this case, a driving state in the drive unit 22 and an orientation of the slave joint 26 are misaligned with each other in a relationship different from an initial corresponding relationship. In this case, the operator can solve the displacement of the corresponding relationship between the master joint 7 and the slave joint 26 by setting the initial position as follows. The plurality of joint elements 8 of the master manipulator 2 has a shape similar to the joint elements 27 of the slave manipulator 20

The initial position is set in a state where the slave arm 21 and the slave overtube 37 is inserted into the body.

In order to treat the treatment target region, the slave manipulator 20 is inserted into the body (Step S11 shown FIG. 6). In the present embodiment, the slave manipulator 20 is inserted into the body via a natural opening such as an anus, for example.

In a state where the endoscope 100 visibly captures a treatment target region X1 (for example, refer to FIG. 4), the slave arm 21 for treating the treatment target region X1 is inserted into the second lumen 40. The end effector 33 and the slave joint 26 of the slave arm 21 are located in the vicinity of a distal end 40a of the second lumen 40. Before the treatment starts in order to treat the treatment target region X1, the end effector 33 and the slave joint 26 of the slave arm 21 are located inside the second lumen 40 of the tube body 38 of the slave overtube 37. In a process of inserting the slave arm 21 into the second lumen 40, the attaching and detaching portion 24 and the power source unit 23 are not connected to each other, and the slave joint 26 is freely transformable to follow a shape of the second lumen 40. In addition, the control unit 50 is controlled not to output an operation command to the power source unit 23 until the initial position is set. In this manner, in a process of attaching the attaching and detaching portion 24 to the power source unit 23, the slave joint 26 is not operated, and follows the shape of the second lumen 40.

Subsequently, the operator observes the vicinity of the treatment target region X1 through the endoscope 100. If necessary, the operator moves the tube body 38 up to a portion where the vicinity of the distal end 38a of the tube body 38 can be brought into a straight state. For example, the shape in the vicinity of the distal end 38a of the tube body 38 can be brought into the straight state by bringing an active bending portion arranged in an insertion portion of the endoscope 100 into a straight state. In the present embodiment, in a region in the vicinity of the distal end 38a of the tube body 38, it is preferable that a region where the slave joint 26 is located is brought into the straight state. In addition, the vicinity of the distal end 38a of the tube body 38 does not need to have a strictly straight shape.

When the vicinity of the distal end 38a of the tube body 38 is substantially straight, the vicinity of the distal end 40a of the second lumen 40 is also substantially straight. Therefore, the slave joint 26 in the second lumen 40 is substantially straight.

Next, the operator of the master manipulator 2 disposes the master arm 4 inside the channel member 16 of the master overtube 15 (refer to FIG. 3). The master arm 4 may be moved to the channel member 16 of the master overtube 15 before or after the slave arm 21 is attached to the second lumen 40. In this case, the master joint 7 is operated so that the master joint 7 is located inside the channel member 16.

Since the channel member 16 is a tubular member having a straight shape, the master joint 7 arranged inside the channel member 16 also follows a straight shape.

In this way, the slave joint 26 is located inside the second lumen 40, and the master joint 7 is located inside the channel member 16, thereby causing both the master joint 7 and the slave joint 26 to have a straight shape.

When the master joint 7 and the slave joint 26 are in the above-described state where both of these have the straight shape, the control unit 50 defines a corresponding relationship between the position of each joint element 8 of the master joint 7 and the position of each joint element 27 of the slave joint 26, as an initial position, and the control unit 50 stores the corresponding relationship. In the present embodiment, when the master joint 7 and the slave joint 26 are in the above-described state where both of these have the straight shape, for example, notification thereof is delivered from the master manipulator 2 to the control unit 50 by using a switch. In this manner, the operator manually starts to define and store the initial position. Based on the above-described notification, the control unit 50 detects whether the channel member 16 is attached to the master manipulator 2, and defines and stores the corresponding relationship between the position of each joint element 8 of the master joint 7 and the position of each joint element 27 of the slave joint 26, as the initial position (Step S12 shown in FIG. 6).

If the initial position is stored, the master arm 4 is moved to the work table 3 so as to cause the input t 14 and the master joint 7 to protrude from the channel member 16 (refer to FIG. 2). Following the operation of the input unit 14 and the master joint 7 which protrude from the channel member 16, the end effector 33 and the slave joint 26 of the slave arm 21 protrude from the distal end of the second lumen 40 (refer to FIG. 5).

The slave arm 21 can be operated at the position of each joint element 27 as an original point when the slave joint 26 is straightly located inside the second lumen 40. That is, if the operator grips the input unit 14 arranged in the master arm 4 and operates the master joint 7, the slave joint 26 is operated to follow the operation of the master joint 7.

The operator treats the treatment target region X1 (refer to FIG. 5) by using the input unit 14 arranged in the master arm 4 (Step S13 shown in FIG. 6).

In some cases, the initial position is reset during the treatment.

For example, as shown in FIG. 7, when a certain desired treatment starts (Step S21 shown in FIG. 7) and the treatment is progressively performed, in a case where there is a difference in the orientation of the end effector 33 of the slave manipulator 20 compared to the input unit 14 of the master manipulator 2 (YES in Step S22 shown in FIG. 7), the initial position is reset (Step S23 shown in FIG. 7).

As shown in FIG. 8, in order to reset the initial position, the master arm 4 is pulled into the channel member 16 (Step S31), and tension of a wire (not shown) of the drive unit 22 is initialized (Step S32). As an example of a method of initializing the tension of the wire, in Step S32, the attaching and detaching portion 24 is detached from the power source unit 23, and thereafter, the attaching and detaching portion 24 is attached to the power source unit 23 again. The drive unit 22 may have a known configuration for maintaining the tension of the wire to be constant.

A state of the drive unit 22 after the tension of the wire is initialized is set as the initial position (Step S33). Thereafter, if the master arm 4 is protruded again from the distal end 16a of the channel member 16, an orientation of the end effector 33 of the slave manipulator 20 becomes an orientation properly following the input unit 14 of the master manipulator 2.

When the treatment using the slave arm 21 is completed (YES in Step S24 shown in FIG. 7), the slave manipulator 20 shown in FIG. 5 is removed from the body (Step S25). In Step S25, first, the master arm 4 is moved to the work table 3 in order to pull the slave arm 21 back into the slave overtube 37. The master arm 4 is pulled into the channel member 16 of the master overtube 15 since the master arm 4 is moved to the work table 3 (refer to FIG. 2). Since the master arm 4 is pulled into the channel member 16, the master joint 7 of the master arm 4 is corrected into a straight shape. The slave joint 26 operated to follow the operation of the master joint 7 becomes since the slave joint 26 follows the straight shape of the master joint 7 (refer to FIG. 4). Therefore, the slave arm 21 is smoothly pulled into the second lumen 40 of the slave overtube 37. As a result, the slave joint 26 is pulled into the slave overtube 37 while being in a bent state. Accordingly, there is no possibility that the slave joint 26 may be damaged.

In addition, only a portion on the proximal side of each joint element (the first joint element 9, the second joint element 10, and the third joint element 11) of the master joint 7 is accommodated inside the channel member 16. The slave manipulator 20 can be operated by using the master manipulator 2 even in a state where the joint element and the end effector 33 of a portion on the distal end side of the master joint 7 protrude from the channel member 16. In this case, in all of the slave joints 26 of the slave manipulator 20, a portion corresponding to the master joint 7 protruding from the channel member 16 can be driven.

As described above, in the manipulator system 1 according to the present embodiment, the slave overtube 37 to be inserted into the body and the master overtube 15 arranged in the master manipulator 2 can easily define the initial position of the slave joint 26 in a state where the slave manipulator 20 is located in the vicinity of the treatment target region.

As a result, according to the manipulator system 1 of the present embodiment, it is possible to easily perform calibration with a simple configuration.

Second Embodiment

Figure 9:
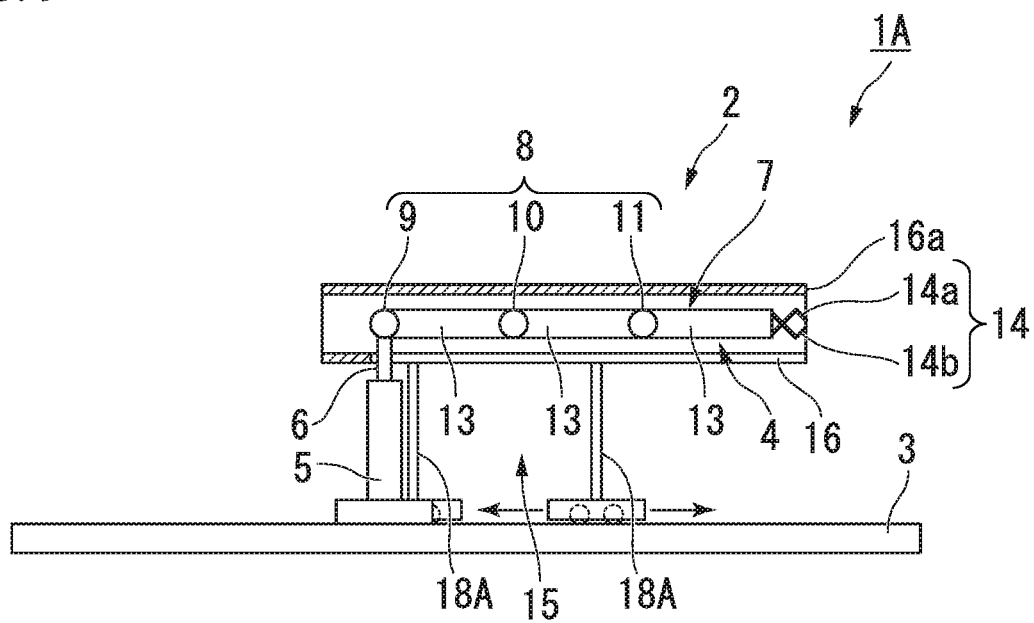
FIG. 9 is a partial sectional view schematically illustrating a partial configuration of a medical master-slave manipulator system according to a second embodiment of the present invention.

A second embodiment according to the present invention will be described. FIG. 9 is a partial sectional view schematically illustrating a partial configuration of a medical master-slave manipulator system 1A according to the present embodiment.

As shown in FIG. 9, in the present embodiment, instead of including the fixing portion 18 disclosed in the first embodiment, the master overtube 15 includes a movable carriage 18A (base) which is movable with respect to the work table 3.

In the present embodiment, the master overtube 15 is moved with respect to the work table 3, thereby enabling the position of the channel member 16 to be adjusted with respect to the master arm 4. For example, it is possible to align the positional relationship of the master arm 4 with the channel member 16 of the master manipulator 2, corresponding to the positional relationship of the slave arm 21 with respect to the second lumen 40 of the slave manipulator 20.

In addition, the work table 3 may be moved to the master overtube 15. In this case, the position of the channel member 16 can also be adjusted with respect to the master arm 4.

Third Embodiment

Figure 11:
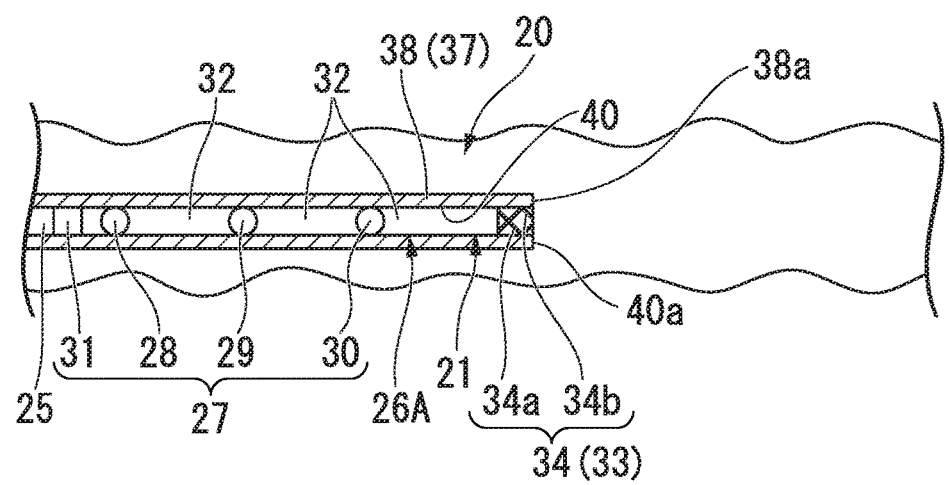
FIG. 11 is a partial sectional view schematically illustrating a portion of a slave manipulator in the manipulator system according to the embodiment.

A third embodiment according to the present invention will be described. 10 is a partial sectional view schematically illustrating a portion of a master manipulator of a medical master-slave manipulator system 1B according to the present embodiment. FIG. 11 is a partial sectional view schematically illustrating a portion of the slave manipulator in the manipulator system 1B.

Figure 10:
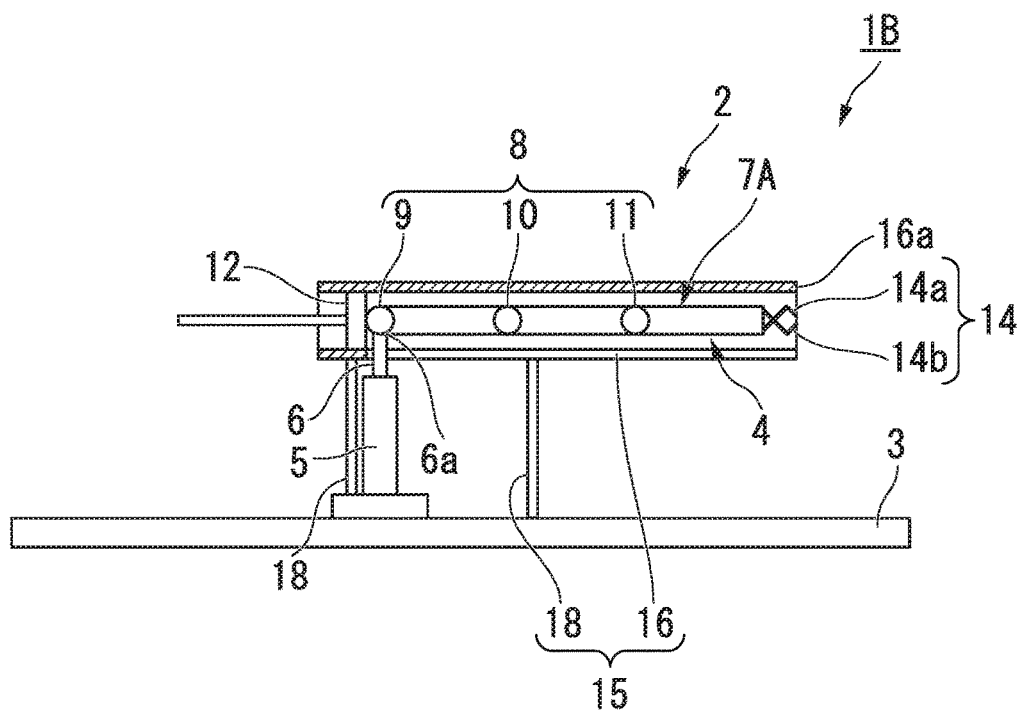
FIG. 10 is a partial sectional view schematically illustrating a portion of a master manipulator of a medical master-slave manipulator system according to a third embodiment of the present invention.

As shown in FIGS. 10 and 11, the medical master-slave manipulator system 1B has a master joint 7A and a slave joint 26A which have a configuration different from that of the master joint 7 and the slave joint 26 which are disclosed in the above-described first embodiment.

As the joint element 8 connecting the shaft 6 and the master joint 7A to each other, the master joint 7A according to the present embodiment has a master side roll shaft joint 12 which rotates the master joint 7A around the distal end 6a of the shaft 6.

The master side roll shaft joint 12 enables the input unit 14 and the master joint 7A to be rotated with respect to the shaft 6. In addition, the master side roll shaft joint 12 has rotation amount detection portion including an encoder (not shown) for detecting a rotation amount of the master side roll shaft joint 12, and a rotation amount measurement portion for enabling the operator to visually measure the rotation amount of the master joint 7A and the input unit 14 which are rotated by the master side roll shaft joint 12.

For example, the rotation amount measurement portion includes a configuration in which a portion of an outer wall of the channel member 16 is transparent in the vicinity of the distal end 16a of the channel member 16 and which has a scale at each predetermined angle in the circumferential direction of the channel member 16, and a configuration which has a sensor for measuring the rotation amount of the master joint 7A or the input unit 14 with respect to the channel member 16 and which displays the rotation amount on the display device 19.

As the joint element 27 connecting the elongated member 25 and the slave joint 26A to each other, the slave joint 26A according to the present embodiment has a slave side roll shaft joint 31 which rotates the slave joint 26 around a center line of the elongated member 25.

The slave side roll shaft joint 31 is operated in response to an operation command from the control unit 50 by a wire (not shown) extending from the drive unit 22 to the slave joint 26A.

In the present embodiment, if the master side roll shaft joint 12 of the master joint 7A is rotated, the slave side roll shaft joint 31 is operated to follow the operation of the master side roll shaft joint 12.

According to the present embodiment, the rotational position of the end effector 33 and the slave joint 26A can be recognized by observation using the endoscope 100 attached to the first lumen 39 arranged in the slave overtube 37.

An example of calibration in the manipulator system 1H according to the present embodiment will be described.

In the present bodiment, in a state where the slave arm 21 is attached to the inside of the second lumen 40, the rotation position of the end effector 33 and the slave joint 26A which are rotated around the center line (center line of the elongated member 25) of the slave arm 21 and the rotational position of the input unit 14 and the master joint 7A which are rotated around the center line (center line of the overall master joint 7 when the master joint 7 is straight) of the master arm 4 are not aligned with each other in some cases.

In this case, in a state where an output of the operation command is stopped from the control unit 50 to the drive unit 22, the master side roll shaft joint 12 rotates the master joint 7A and the input unit 14 around the above-described center line of the master arm 4. In this manner, the rotation position of the input unit 14 and the master joint 7A can be aligned with the rotation position of the end effector 33 and the slave joint 26A.

In the present embodiment, the endoscope 100 is used for the observation. In this manner, an angle of the end effector 33 and the slave joint 26A in the circumferential direction of the second lumen 40 is recognized. A scale arranged in the channel member 16 is used. In this manner, the slave side roll shaft joint 31 is rotated with respect to the channel member 16 so as to be aligned with the angle of the end effector 33 and the slave joint 26A.

Accordingly, it is possible to easily perform calibration to solve the displacement in the rotational direction of the input unit 14 and the master joint 7A with respect to the end effector 33 and the slave joint 26A.

In addition, according to the present embodiment, even in a case where the slave arm 21 does not have a joint rotating around a roll axis, the displacement can be solved by rotating the master side roll shaft joint 12 in a case of the displacement in the rotation direction of the master arm 4 with respect to the slave arm 21.

Fourth Embodiment

Figure 12:
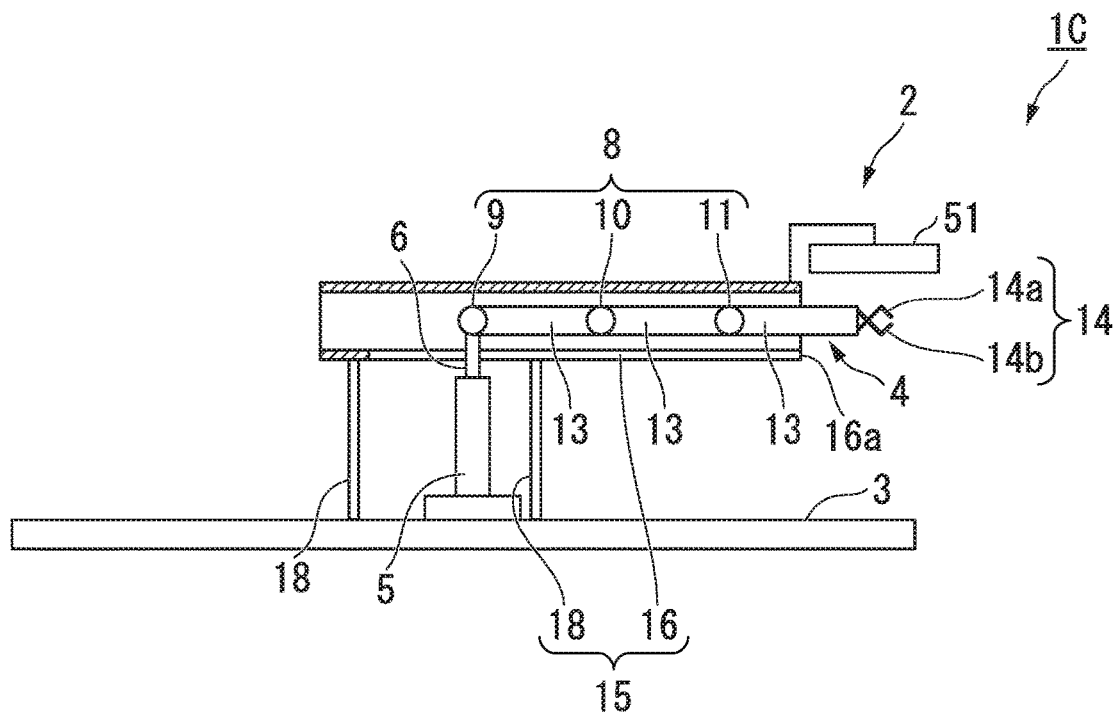
FIG. 12 is a partial sectional view schematically illustrating a portion of a master manipulator of a medical master-slave manipulator system according to a fourth embodiment of the present invention.
Figure 13:
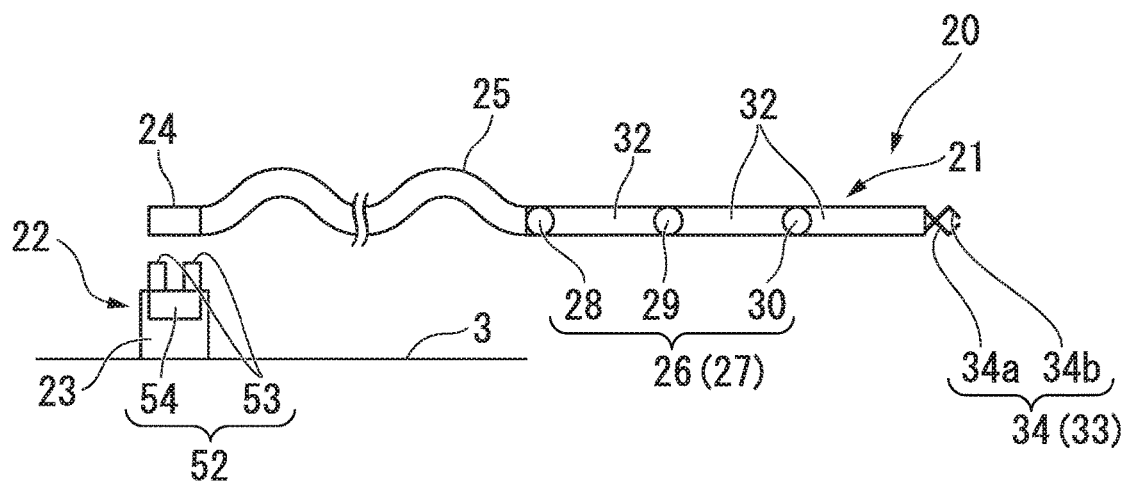
FIG. 13 is a schematic view illustrating a portion of a slave manipulator in the manipulator system according to the embodiment.

A fourth embodiment according to the present invention will be described. FIG. 12 is a partial sectional view schematically illustrating a portion of a master manipulator of a medical master-slave manipulator system 1C according to the present embodiment. FIG. 13 is a schematic view illustrating a portion of a slave manipulator in the manipulator system 1C.

As shown in FIGS. 12 and 13, the medical master-slave manipulator system 1C includes a position sensor 51 and a detachment switching mechanism 52 in addition to the manipulator system 1 disclosed in the above-described first embodiment. The position sensor 51 detects whether or not a position of the master arm 4 is a predetermined position with respect to the channel member 16 in a direction of the center line of the channel member 16. The detachment switching mechanism 52 allows or inhibits an attachment/detachment operation between the attaching and detaching portion 24 and the power source unit 23 in response to a detection state of the position sensor 51.

In addition, he control unit 50 of the medical master-slave manipulator system 1C controls the operation of the detachment switching mechanism 52 in response to the detection state of the position sensor 51.

The position sensor 51 issues a predetermined signal which can be referred to by the control unit 50 when the input unit 14 protrudes from the distal end 16a of the channel member 16. For example, the position sensor 51 issues the above-described signal in a case where a space in the vicinity of the distal end 16a of the channel member 16 is set as a predetermined detection area and where an object is present in this detection area.

In the power source unit 23, the detachment switching mechanism 52 has a regulating member 53 which can enter a portion of the attachment/detachment position of the attaching and detaching portion 24, and a movement unit 54 which moves the regulating member 53 in accordance with the control from the control unit 50. In a state where the regulating member 53 enters the attachment/detachment position, the attaching and detaching portion 24 cannot be attached to the power source unit 23.

When the control unit 50 detects that the position sensor 51 issues the above-described predetermined signal, the control unit 50 controls the detachment switching mechanism 52 so that the regulating member 53 enters the attachment/detachment position. In addition, when the control unit 50 detects that the position sensor 51 stops issuing the above-described predetermined signal, the control unit 50 moves the regulating member 53 out from the attachment/detachment position.

In the present embodiment, in a case where the control unit 50 determines that the input unit 14 is located inside the channel member 16, the control unit 50 allows the attaching and detaching portion 24 to be attached to the power source unit 23. Conversely, in a case where the control unit 50 determines that the input unit 14 protrudes outward from the distal end 16 of the channel member 16, the control unit 50 inhibits the attaching and detaching portion 24 from being attached to the power source unit 23.

In a state where the input unit 14 is located inside the channel member 6, the master joint 7 is also located inside the channel member 16. Accordingly, the master joint 7 is in a straight state for suitably performing the calibration disclosed in the first embodiment. In a state where the input unit 14 protrudes from the distal end 16a of the channel member 16, the input unit 14 or the master joint 7 protrudes to the outside of the channel member 16 from the distal end 16a of the channel member 16. Consequently; it is conceivable that the master joint 7 is not in a suitably straight state.

According to the present embodiment, only in a case where taster joint 7 is located inside the channel member 16 after being brought into the suitably straight state, the power source unit 23 and the attaching and detaching portion 24 are allowed to be connected to each other. Therefore, it is possible to prevent the calibration from being performed while the position relationship is not suitable for the calibration.

Hitherto, the embodiments according to the present invention have been described in detail with reference to the drawings. However, a specific configuration is not limited to these embodiments, and the design can be changed within the scope not departing from the gist of the present invention.

In addition, the configuration elements described in the above-described respective embodiments can be appropriately combined with each other for an alternative configuration.

The invention claimed is:

1. A medical master-slave manipulator system comprising:
    a slave manipulator which has an end effector and a joint;
    a master manipulator which has a joint having a shape similar to the joint of the slave manipulator, and which receives an operation input for operating the slave manipulator;
    a control unit that generates an operation command for operating the slave manipulator based on the operation input to the master manipulator, and outputs the operation command to the slave manipulator;
    an overtube which has a tubular shape and into which the slave manipulator is inserted; and
    a correction jig that has a shape similar to at least a portion of the overtube so as to correct the master manipulator into a shape following an internal shape of the overtube, and that is attachable to the master manipulator,
    wherein in a state where the correction jig is attached to the master manipulator, the correction jig limits the joint of the master manipulator to be a straight state.

2. The medical master-slave manipulator system according to claim 1,
    wherein when the control unit detects that the correction jig is attached to the master manipulator, the control unit generates the operation command for relatively moving the slave manipulator and the overtube so that the slave manipulator moves into the overtube and outputs the operation command to the slave manipulator, and
    wherein in a state where the slave manipulator is located inside the overtube and the correction jig is attached to the master manipulator, the control unit sets a position of the joint of the slave manipulator which corresponds to the joint of the master manipulator, as an origin position of the joint in the slave manipulator.

3. The medical master-slave manipulator system according to claim 1,
    wherein the correction jig has
    a channel member that holds the joint of the master manipulator to be a shape following a shape of the joint of the slave anipulator arranged inside the overtube, and
    a base that moves the channel member with respect to the master manipulator.

4. The medical master-slave manipulator system according to claim 1,
    wherein the correction jig has a channel member that holds the joint of the master manipulator to be a shape following a shape of the joint of the slave manipulator arranged inside the overtube, and a base that holds the channel member, and
    wherein the master manipulator is movable to the channel member so that at least the joint of the master manipulator is attached to the channel member.

5. The medical master-slave manipulator system according to claim 4,
    wherein the master manipulator has a work table and a master arm that has an input unit which corresponds to the end effector, and the joint of the master manipulator, and
    wherein the channel member is arranged on the work table so as to be relatively movable with respect to the master arm and so as to be capable of being fixed to the master am in a state where the master arm is positioned with respect to the work table.

6. The medical master-slave manipulator system according to claim 1,
    wherein the correction jig has a channel member into which the master manipulator is capable being inserted and which has a shape similar to the overtube, and a rotation amount measurement portion which is configured to measure a rotation amount of the master manipulator rotating in a circumferential direction of the channel member in the channel member.

7. The medical master-slave manipulator system according to claim 1,
    wherein when the control unit is actuated, the control unit determines whether or not the correction jig is in a positional relationship that the correction jig is attached to the master manipulator, and in a case where the correction jig is not in a positional relationship that the correction jig is attached to the master manipulator, the control unit stops controlling the slave manipulator until the correction jig is in the position relationship that the correction jig is attached to the master manipulator.

8. A medical master-slave manipulator system in which an operation for operating the slave manipulator including an end effector and a slave joint is input, the medical master-slave manipulator system comprising:
    a first arm which is formed in a rod shape;
    a second arm which is formed in a rod shape;
    a master joint which is connected to the first arm and the second arm such that the first arm and the second arm are capable of bending with respect to each other; and
    a correction jig which limits a bend of the second arm with respect to the first arm.

9. The medical master-slave manipulator system according to claim 8, the correction jig includes a tube in which the first arm and the second arm are capable of being inserted, and the correction jig limits the bend of the second arm with respect to the first arm by the first arm and the second arm being inserted into the tube.

\* \* \* \* \*